United States Patent [19]

Liu

[11] Patent Number: 4,569,841

[45] Date of Patent: Feb. 11, 1986

[54] *ERWINIA HERBICOLA* STRAIN THAT INHIBITS PATHOGENIC PLANT BACTERIA

[75] Inventor: Shih-Tung Liu, Davis, Calif.

[73] Assignee: Chevron Research Company, San Francisco, Calif.

[21] Appl. No.: 503,379

[22] Filed: Jun. 10, 1983

[51] Int. Cl.[4] .................... A01N 63/00; A01G 13/00; C07G 17/00

[52] U.S. Cl. ............................. 424/93; 47/2; 435/267; 435/800; 435/847; 435/253

[58] Field of Search ............... 435/847, 253, 267, 800, 435/170, 240; 424/93; 47/2

[56] References Cited

U.S. PATENT DOCUMENTS

| | | | |
|---|---|---|---|
| 4,045,910 | 9/1977 | Arny et al. | 47/2 |
| 4,161,084 | 7/1979 | Anny et al. | 47/2 |
| 4,432,160 | 2/1984 | Lindow | 47/2 |

OTHER PUBLICATIONS

Bergey's Manual of Determinative Bacteriology, 8th Ed, 1974, pp. 333–336.

*Primary Examiner*—Sam Rosen
*Assistant Examiner*—William J. Herald
*Attorney, Agent, or Firm*—J. A. Buchanan, Jr.; T. G. DeJonghe

[57] ABSTRACT

A strain of *Erwinia herbicola* identified as EHO-10 has been found to have a broad spectrum of inhibitory activity against pathogenic bacteria. Pathogenic bacteria inhibited by EHO-10 includes those from the following genera: Agrobacterium, Corynebacterium, Erwinia, Pseudomonas, and Xanthomonas. EHO-10 has inhibitory activity against *Erwinia amylovora*, a bacteria pathogen causing fire blight disease of pear and other trees.

4 Claims, No Drawings

ERWINIA HERBICOLA STRAIN THAT INHIBITS PATHOGENIC PLANT BACTERIA

FIELD OF THE INVENTION

This invention relates to a microorganism useful in the control of fire blight, a disease that damages pear and apple trees, and also useful in the control of other bacterially induced plant diseases.

BACKGROUND OF THE INVENTION

It is generally accepted that the bacterial diseases of plants are difficult to control. Usually a combination of methods, such as the use of chemicals, antibiotics, sanitation practices, and the use of clean seed stock, are used in combination to control bacterial diseases of plants.

Plant pathogenic bacteria include those from the following genera: Agrobacterium, Corynebacterium, Erwinia, Pseudomonas, Xanthomonas, and Streptomyces.

Example diseases caused by these bacteria include wild fire of tobacco, caused by *P. tabaci;* canker of stone fruit and pome fruit trees as well as citrus blast, pear blast, bean leaf spot and lilac blight, all caused by *P. syringae;* common blight of beans, caused by *X. phaseoli;* crown gall of (woody) plants, such as stone fruits, pome fruits and grape, caused by *A. tumafaciens;* bean wilt, caused by *C. flaccumfaciens;* wilting and cankering of tomato plants, caused by *C. michiganense;* soft rot of fleshy fruits, caused by *E. carotovora;* and fire blight of pear and apple trees, caused by *E. amylovora.*

The use of bacteria to control pathogenic bacteria has been disclosed. For example, W. O. Reil et al. in California Agriculture, April 1974, pages 4-6 disclosed the use of an antagonistic bacteria mixture to control *E. amylovora.* Reil et al. found that although greater control was achieved using a chemical bactericide, the bacteria control method gave some positive control.

S. D. Beer et al. in Phytopathology 70:459 (1980) disclosed the use of *E. herbicola* bacteria to control *E. amylovora* in apple trees.

S. V. Thompson et al. obtained approximately equal control in the field of pear tree fire blight bacteria (*E. amylovora*) using bacteria vs. using chemical bactericides, Phytopathology, December 1976, Vol. 66, page 1457. Thompson et al. used a mixture of three species of Pseudomonas and one Erwinia bacteria species to control *E. amylovora* pathogenic bacteria. The Erwinia species used by Thompson et al. for their field study produced, in preliminary laboratory studies, an inhibition zone against *E. amylovora* but not against *P. syringae* nor did it produce inhibition against *E. carotovora* var. *atroseptica* nor against *E. carotovora* var. *carotovora.*

SUMMARY OF THE INVENTION

According to the present invention a biologically pure bacterium is provided which controls a broad spectrum of bacterial diseases of plants.

The subject bacteria is herein identified as *E. herbicola* strain EHO-10. This bacterial strain is also further identified below by ATCC number.

Among other factors, the present invention is based on my finding that EHO-10 has a surprisingly broad spectrum of inhibition or antagonism against plant pathogenic bacteria. That is, several different plant pathogenic bacteria are inhibited in growth by the subject bacteria. Genera of plant pathogenic bacteria which I have found inhibited in growth by EHO-10 include: Agrobacterium, Corynebacterium, Erwinia, Pseudomonas, and Xanthomonas.

The inhibition is effectuated, it is believed, by a bactericide made by the bacterium EHO-10, but for ease of reference herein, typically the inhibition is simply treated as coming from the EHO-10 bacteria.

The present invention embraces not only the bacterium EHO-10, in its biologically pure culture form, but also the use of this bacterium to inhibit strains of bacteria from any one or more of the foregoing plant pathogenic bacteria genera. The present invention also embraces the bactericide from EHO-10, which is effective for inhibiting strains of bacteria from any one or more of the foregoing pathogenic bacteria genera; and the use of such bactericide to inhibit such pathogenic bacteria.

It is particularly preferred to use the EHO-10 bacterium of the present invention for inhibition of the following strains of plant pathogenic bacteria: *E. amylovora, C. flaccumfaciens, C. michiganense, P. syringae, P. glycinea, E. carotovora, E. chrysanthemi, X. vitians,* and *X. alfalfae.*

Preferably the EHO-10 bacteria, or the effective bactericidal compound produced by it, is applied to the plant carrying the pathogenic bacteria by spraying onto the plant in areas of the habitat of the pathogenic bacteria. Thus, for control of fire blight, it is preferred to spray the bacteria onto the blossoms of the pear or apple tree.

Preferred concentrations will be adjusted according to the particular application in field conditions. For fire blight control preferred concentrations of bacteria are between $10^7$ and $10^9$ colony forming units per milliliter of aqueous spray solution, and preferred application time is in the Spring, most preferably in March, when 50 to 100% of the blossoms are in bloom. Preferably, a second spray is applied 1-2 days after the first spray.

A cultured deposit of EHO-10 has been made at American Type Culture Collection, 1230 Park Lawn Drive, Rockville, Maryland 20852 and identified by ATCC No. 39368.

EXAMPLES

Various strains of *E. herbicola* were obtained and tested against certain pathogenic bacteria.

Table I below lists the various strains of *E. herbicola* which were tested. The second column in Table I lists standard api 20E test results for the various test strains. Table II lists taxonomic data in more detail for *E. herbicola* strain EHO-10. Table III lists pathogenic bacteria against which the various strains of *E. herbicola* were tested. Also, the plant disease induced by the pathogenic bacteria is shown in Table II.

The *E. herbicola* strains were maintained on 179 agar which has the following composition on a per liter basis: 8 g of casein enzyme hydrolysate, 4 g of yeast extract, 4 g of $K_2HPO_4$, 4 g of $KH_2PO_4$, 0.3 g of $MgSO_4.7H_2O$, 33.2 mg of bromcresol purple (in ethanol), and 20 g of agar.

For the in vitro antagonism bioassay *Erwinia amylovora* and *E. herbicola* were grown in L Broth which has the following composition on a per liter basis: 10 g of Bacto tryptone, 5 g of Bacto yeast extract, 10 g of NaCl, and 1 drop of antifoam, pH 7.2-7.4.

Tests of the antagonism of various strains of *E. herbicola* against pathogenic bacteria were carried out as follows:

Ten microliters of a log phase culture of the antagonist (E. herbicola) was spotted onto the center of an NAG (Difco Nutrient agar supplemented with 0.5% glucose) petri plate or an MB agar plate (per liter: 2 g K₂HPO₄, 2 g NaCl, 1 g Na citrate, 0.6 g Asparagine, 24 g Potato Dextrose broth, 18 g agar) with a micropipet and incubated at 29° C. for 48 hours. An LB culture of E. amylovora was then oversprayed with a mechanical sprayer and the plates were incubated an additional 18-24 hours prior to scoring.

The results were obtained by measuring the area of the inhibition zone and dividing it by the area of the colony of the antagonistic bacterium. These area ratios are reported in Tables IV, V and VI.

Table IV lists results of the tests of various strains of E. herbicola when oversprayed with various pathogenic bacteria. The pathogenic bacteria oversprayed are listed at the top of each column. The results for the respective strains of E. herbicola are shown in horizontal position opposite the respective E. herbicola strains. As can be seen from the data, EHO-10 was especially effective in inhibiting the growth of a wide spectrum of pathogenic bacteria. EHO-10 was more than twice as effective as any of the other strains of E. herbicola in inhibiting the growth of E. amylovora.

Table V lists results for similarly conducted tests except that in all of the Table V tests the pathogenic bacterium oversprayed was E. amylovora. The particular E. amylovora strain used is designated Eam 5. The results in Table V show again that E. herbicola strain 10 is particularly effective in inhibiting the growth of E. amylovora.

Table VI lists results for similarly conducted tests except for a wider range of pathogenic bacteria. The pathogenic bacteria are shown in the first column. The strain of E. herbicola tested for inhibition effectiveness is shown in the second column. The third column tabulates the ratio of the area of inhibition to the colony size of the E. herbicola strain in the petri dish. The results shown in Table VI illustrate inhibition activity for E. herbicola strain 10 against a broad spectrum of pathogenic bacteria.

TABLE I

| Lab. Code No. | api Test | Original Designation | Source |
|---|---|---|---|
| EHO-1 | 1004513 | 25D31 | Dr. C. I. Kado, U.C. Davis |
| EHO-2 | 1004513 | 25D32 | Dr. C. I. Kado, U.C. Davis |
| EHO-3 | 1004533 | 25D3 | Dr. C. I. Kado, U.C. Davis |
| EHO-4 | — | — | Dr. C. I. Kado, U.C. Davis |
| EHO-5 | 1004133 | 25D35 | Dr. C. I. Kado, U.C. Davis |
| EHO-6 | 1004533 | 25D36 | Dr. C. I. Kado, U.C. Davis |
| EHO-7 | 1004533 | 25D37 | Dr. C. I. Kado, U.C. Davis |
| EHO-8 | 1004533 | 25D38 | Dr. C. I. Kado, U.C. Davis |
| EHO-9 | 1004133 | 25D39 | Dr. C. I. Kado, U.C. Davis |
| EHO-10 | 1004553 | 11LP-1 | Apple Leaf, Fresno |
| EHO-11 | 1044173 | 1L-4 | Pear Leaf, Placerville |
| EHO-12 | 1004133 | 3L2-1 | Apple Leaf, Placerville |
| EHO-13 | 124473 | 6B-1 | Pear Bud, Placerville |
| EHO-14 | 1004713 | 4B-2 | Apple Bud, Placerville |
| EHO-15 | 1004133 | 3B-2 | Apple Bud, Placerville |
| EHO-16 | 1004133 | 3B-2-1 | Apple Bud, Placerville |
| EHO-17 | 1004372 | 3B-1 | Apple Bud, Placerville |
| EHO-18 | 1004133 | 12-2 | Apple Leaf, Fresno |
| EHO-19 | 1004353 | 12-1 | Apple Leaf, Fresno |
| EHO-20 | 1004133 | 4L2-1 | Apple Leaf, Placerville |
| EHO-21 | 1004173 | 37-2 | Apple Bud, Fresno |
| EHO-22 | 1004132 | 38-2 | Apple Bud, Fresno |
| EHO-23 | 1004132 | 40-1 | Apple Bud, Fresno |
| EHO-24 | | 2B-2 | — |

TABLE II

| Taxanomy Data for EHO-10 | |
|---|---|
| Original Isolation No.: | 11LP-1 |
| Host Plant: | Apple |
| Location of Isolation: | Fresno Field Station |
| Date: | December 1981 |
| Isolated by: | Keith Perry |
| api No.: | 1004553 which codes for an equivalent of E. herbicola |
| Characteristics: | 1. Gram negative |
| | 2. Short rod |
| | 3. Motile |
| | 4. Oxidase negative |
| | 5. Oxidative and fermentative metabolism of glucose |
| | 6. Produce yellow pigment on LB or nutrient agar |
| | 7. Vogue-Proskauer test negative |
| | 8. Grows on MacConkey agar |
| | 9. Grows at 37° C. |
| | 10. Plasmid molecular weights: 25, 64, 72 megadaltons |
| api 20E Test for EHO-10 | |
| 1. ONPG | + beta-glatosidase |
| 2. ADH | − Arginine dihydrolase |
| 3. LDC | − Lysine decarboxylase |
| 4. ODC | − Ornithine decarboxylase |
| 5. CIT | − Citrate utilization |
| 6. H₂S | − Hydrogen sulfide production |
| 7. URE | − Production of ammonia from urea |
| 8. TDA | − Production of indolepyruvate |
| 9. IND | − Production of indole |
| 10. VP | − Production of acetoin |
| 11. GEL | − Liquefaction of gelatin |
| 12. GLU | + Utilization of glucose |
| 13. MAN | + Utilization of mannitol |
| 14. INO | − Utilization of inositol |
| 15. SOR | + Utilization of sorbitol |
| 16. RHA | + Utilization of rhamnose |
| 17. SAC | − Utilization of sucrose |
| 18. MEL | + Utilization of melibiose |
| 19. AMY | + Utilization of amygdalin |
| 20. ARA | + Utilization of (1+) arabinose |
| 21. Oxidase | − Presence of cytochrome oxidase |

The api results were read after 48 hours of incubation at 28° C.

TABLE III

| Pathogen | Disease Induced |
|---|---|
| C. flaccumfaciens | Bacterial wilt of bean |
| C. michiganense | Tomato canker and wilt |
| P. syringae | Blasts, blights, cankers of many hosts |
| P. glycinea | Soybean bacterial blight |
| E. carotovora | Soft rot of many vegetables in field and storage |
| E. chrysanthemi | Bacterial blight of chrysanthemum |
| A. tumefaciens | Crown galls |
| E. amylovora | Fire blight of pear trees, etc. |

TABLE IV

| E. herbicola Strain | A | B | C | D | E |
|---|---|---|---|---|---|
| EHO-1 | 1.40* | 1.69* | 2.27* | 2.22* | 1.64* |
| EHO-2 | 1.17 | 1.97 | 1.96 | 2.27 | 1.41 |
| EHO-3 | 1.97 | 4.01 | 3.89 | 3.62 | 1.99 |
| EHO-5 | 1.32 | 4.01 | 3.61 | 3.65 | 3.12 |
| EHO-6 | 1.47 | 2.48 | 2.33 | 3.03 | 1.75 |
| EHO-7 | 1.69 | 2.15 | 2.33 | 2.21 | 0 |
| EHO-8 | 1.47 | 2.31 | 2.78 | 3.75 | 0 |
| EHO-9 | 0 | 0 | 0 | 0 | 0 |
| EHO-10 | 12.56 | 14.38 | 13.21 | 15.37 | 10.86 |
| EHO-11 | 7.7 | 4.8 | 7.6 | 5.69 | 3.27 |
| EHO-12 | 3.83 | 2.82 | 0 | 0 | 2.72 |
| EHO-13 | 4.23 | 0 | 0 | 0 | 0 |
| EHO-14 | 6.72 | 10.87 | 9.45 | 6.74 | 6.73 |
| EHO-15 | 1.15 | 0 | 0 | 0 | 0 |

TABLE IV-continued

| E. herbicola Strain | A | B | C | D | E |
|---|---|---|---|---|---|
| EHO-16 | 1.55 | 0 | 0 | 0 | 0 |
| EHO-17 | 0 | 0 | 0 | 0 | 0 |
| EHO-18 | 1.09 | 1.82 | 1.13 | 1.29 | 0 |
| EHO-19 | 5.29 | 12.91 | 8.57 | 12.54 | 9.26 |
| EHO-20 | 1.32 | 0 | 0 | 0 | 0 |
| EHO-21 | 1.57 | 0 | 0 | 0 | 1.5 |
| EHO-22 | 1.69 | 0 | 0 | 1.15 | 0 |
| EHO-23 | 0 | 0 | 0 | 0 | 0 |
| EHO-24 | 1.33 | 0 | 0 | 0 | 0 |

A = Erwinia amylovora
B = Agrobacterium tumefaciens
C = Pseudomonas syringae
D = Xanthomonas campestri
E = Corynebacterium flaccumfaciens
*Area Ratio = area of inhibition zone divided by area of colony size.

TABLE V

| Antagonist | Indicator Strain | Medium | Antagonism | Area* Ratio |
|---|---|---|---|---|
| EHO-1 | Eam 5+ | NAG | + | 1.82 |
| EHO-2 | Eam 5 | NAG | + | 1.77 |
| EHO-3 | Eam 5 | NAG | + | 3.61 |
| EHO-5 | Eam 5 | NAG | − | 0 |
| EHO-6 | Eam 5 | NAG | + | 1.32 |
| EHO-7 | Eam 5 | NAG | + | 2.16 |
| EHO-8 | Eam 5 | NAG | − | 0 |
| EHO-9 | Eam 5 | NAG | − | 0 |
| EHO-10 | Eam 5 | NAG | + | 13.47 |
| EHO-11 | Eam 5 | NAG | + | 12.25 |
| EHO-12 | Eam 5 | NAG | − | 0 |
| EHO-13 | Eam 5 | NAG | − | 0 |
| EHO-14 | Eam 5 | NAG | − | 0 |
| EHO-15 | Eam 5 | NAG | − | 0 |
| EHO-16 | Eam 5 | NAG | + | 1.51 |
| EHO-17 | Eam 5 | NAG | + | 1.51 |
| EHO-18 | Eam 5 | NAG | + | 1.32 |
| EHO-19 | Eam 5 | NAG | + | 1.64 |
| EHO-20 | Eam 5 | NAG | − | 0 |
| EHO-21 | Eam 5 | NAG | − | 0 |
| EHO-22 | Eam 5 | NAG | − | 0 |
| EHO-23 | Eam 5 | NAG | − | 0 |
| EHO-24 | Eam 5 | NAG | − | 0 |

+Eam 5 = Erwinia amylovora strain Eam 5
*Area Ratio = area of inhibition zone divided by area of colony size.

TABLE VI

| Indicator Strain | Antagonist | Area Ratio* |
|---|---|---|
| Erwinia caratovora | EHO-10 | 15.21 |
| | EHO-11 | 3.24 |
| | EHO-19 | 2.02 |
| Pseudomonas syringae 323 | EHO-10 | 11.56 |
| | EHO-11 | 3.24 |
| | EHO-19 | 2.16 |
| Xanthomonas vitians | EHO-10 | 19.36 |
| | EHO-11 | 4.41 |
| | EHO-19 | 5.15 |
| Xanthomonas alfalfae | EHO-10 | 16.81 |
| | EHO-11 | 5.15 |
| | EHO-19 | 2.16 |
| Pseudomonas syringae 5D4214 | EHO-10 | 16 |
| | EHO-11 | 3.61 |
| Corynebacterium michiganense | EHO-10 | 15.21 |
| | EHO-11 | 2.10 |
| Erwinia amylovora Eam 1 | EHO-10 | 8.41 |
| | EHO-11 | 3.80 |
| | EHO-19 | 0 |
| Erwinia amylovora Eam 5 | EHO-10 | 11.56 |
| | EHO-11 | 3.42 |
| | EHO-19 | 1.87 |
| Erwinia amylovora Eam 12 | EHO-10 | 16.40 |
| | EHO-11 | 4.41 |
| | EHO-19 | 3.03 |
| Corynebacterium flaccumfaciens | EHO-10 | 3.24 |
| | EHO-11 | 2.25 |
| | EHO-19 | 0 |
| Erwinia chrysanthemi | EHO-10 | 1.69 |
| | EHO-11 | 1.85 |
| | EHO-19 | 0 |

Source:
The above bacterial strains, except E. amylovora strains, were obtained from University of California, Davis, Plant Pathology culture collections. E. amylovora strains were isolated by my field work in 1981.

What is claimed is:

1. A biologically pure strain of Erwinia herbicola ATCC No. 39368.

2. The inhibition on plants of two or more bacteria from the following plant pathogenic bacteria genera: Agrobacterium, Corynebacterium, Erwinia, Pseudomonas or Xanthomonas by a method which comprises spraying the plants with a liquid medium containing the bacterium of claim 1 in suspension.

3. The inhibition on plants of the following plant pathogenic bacteria: E. amylovora, C. flaccumfaciens, C. michiganense, P. syringae, P. glycinea, E. carotovora, E. chrysanthemi, X vitians, or X. alfalfae by a method which comprises inoculating the plants with the bacterium of claim 1.

4. The inhibition of E. amylovora on plants by a method which comprises spraying the plants with the bacterium of claim 1.

* * * * *